United States Patent [19]
Matsutani et al.

[11] Patent Number: 5,902,320
[45] Date of Patent: May 11, 1999

[54] SURGICAL NEEDLE, PRODUCTION METHOD THEREOF, AND NEEDLE HOLDER

[75] Inventors: Kanji Matsutani; Masatoshi Fukuda; Katsutoshi Sato; Akira Saito, all of Tochigi-ken, Japan

[73] Assignee: Mani, Inc., Tochigi, Japan

[21] Appl. No.: 08/924,659

[22] Filed: Sep. 5, 1997

[30] Foreign Application Priority Data

Feb. 12, 1997 [JP] Japan ........................................ 9-27544

[51] Int. Cl.⁶ .................................................. A61B 17/04
[52] U.S. Cl. ................................ 606/222; 606/223; 163/5
[58] Field of Search ................................... 606/222–224, 606/147; 163/5

[56] References Cited

U.S. PATENT DOCUMENTS

| | | | |
|---|---|---|---|
| 1,327,577 | 1/1920 | Turner | 606/147 |
| 2,706,987 | 4/1955 | Bramstedt | 606/147 |
| 4,074,718 | 2/1978 | Morrison, Jr. | 128/303.14 |
| 5,180,385 | 1/1993 | Sontag | 606/224 |
| 5,222,962 | 6/1993 | Burkhart | 606/147 |
| 5,242,458 | 9/1993 | Bendel et al. | 606/147 |
| 5,549,629 | 8/1996 | Thomas et al. | 606/223 |
| 5,571,101 | 11/1996 | Ellman et al. | 606/45 |

FOREIGN PATENT DOCUMENTS

| | | |
|---|---|---|
| 0500229 | 8/1992 | European Pat. Off. . |
| 43 121 47 A1 | 10/1993 | Germany . |

*Primary Examiner*—Gary Jackson
*Attorney, Agent, or Firm*—Townsend & Banta

[57] ABSTRACT

The present invention provides a surgical needle having a needle tip end and a clamping portion to be clamped by a needle holder for applying a current, wherein

- the needle tip end is made from a conductive material which is electrically connected to a conductive material of the clamping portion,
- an insulating layer is provided over the clamping portion and a tip surrounding portion of the surgical needle, whereas at least the needle tip end is electrically exposed, and
- when the insulating material over the clamping portion is clamped by the needle holder, the conductive material of the clamping portion is electrically connected to the needle holder.

12 Claims, 13 Drawing Sheets

SURGICAL NEEDLE, PRODUCTION METHOD THEREOF, AND NEEDLE HOLDER

BACKGROUND OF THE INVENTION

1. Field of the Invention

The present invention relates to a surgical needle for suturing a tissue in a surgical operation and particularly, to a surgical needle having a significantly small resistance when going through a tissue enabling to reduce strength required of a surgeon and a method for producing the surgical needle as well as a needle holder for holding the needle to be grasped by the surgeon.

2. Description of the Prior Art

The technology to apply a high frequency current between an tip of a surgical needle and a tissue of an organ so as to create a hallow portion for passing the surgical needle is suggested, for example, Japanese Patent Laid-Open Hei 9-19436.

In this technology, a surgical needle is wrapped by insulating means excluding its tip and tail so that the tail is clamped by a needle holder which is connected to a high frequency power source so as to apply a high frequency current to the tip of the surgical needle. The high frequency current is carried between a tissue of an organ and the tip of the surgical needle so as to apply a high temperature heat to a portion where the tip of the surgical needle has approached so that a cavity is created in the tissue, enabling to pass the surgical needle through with a small load applied.

Because a high frequency current is applied to the surgical needle, the tail to be clamped by the needle holder is electrically exposed without any insulating material, and the tail portion to be clamped by the needle holder is predetermined in the design stage.

However, when carrying out a surgical operation in an abdomen of a patient having various complicated organs, a surgeon should handle the surgical needle and the needle holder within a limited range. The aforementioned conventional surgical needle has a problem that it is difficult to handle the surgical needle because a predetermined position of the surgical needle should be clamped by the needle holder and the surgeon cannot move the surgical needle as he/she wishes.

It can also be considered to design the tail portion without insulation larger than usual so as to increase the range of the surgical needle which can be clamped by the needle holder. In such a case, however, the tail of the surgical needle is brought into contact with a tissue of an organ before the tip of the surgical needle has passed through the tissue. In such a state, the high frequency current from the needle holder flows directly into the tissue of the patient so as to heat a portion of the tissue to be left as a cavity. Moreover, this current leak causes insufficient high frequency current applied to the tip of the surgical needle, disabling, in some cases, to pass through the tissue.

It is also considered to prepare a plurality of surgical needles, each having a different length of a tail without insulation so that they can be used according to the actual operation conditions. However, there are various types and various configurations of the surgical needle, and it is practically impossible to vary the tail length for each of the types and each of the configurations.

SUMMARY OF THE INVENTION

It is therefore an object of the present invention to provide a surgical needle having a predetermined range in which any position can be clamped by a needle holder so as to define the range where current passes, so that the needle can easily be manipulated during a surgical operation without causing a current leak except for the tip of the surgical needle and without deteriorating the needling ability.

In order to achieve the aforementioned object, the present invention provides a surgical needle having a tip portion and a clamping portion to be clamped by a needle holder for applying a current, wherein the tip portion and the clamping portion are made of conductive members which are electrically connected to each other, and the clamping portion and a portion in the vicinity of the tip portion have surfaces covered with an insulating material, whereas at least the tip portion is electrically exposed, so that when the insulating member of the clamping portion is clamped by the needle holder, the conductive member of the clamping portion is enabled to be electrically connected to the needle holder.

According to another aspect of the present invention, there is provided a method for producing the aforementioned surgical needle and the needle disclosed in Japanese Patent Laid-Open Hei 9-19436, i.e., a surgical needle having a tip portion which is electrically exposed and a clamping portion which is made of a conductive member which can electrically be connected to a needle holder for applying a current, when the clamping portion is clamped by the needle holder. The method is such that the surface of the surgical needle including at least a tip portion is covered with the insulating material and, after this, a portion of the insulating material covering at least the tip portion is removed so as to electrically expose the tip portion.

According to still another aspect of the present invention, there is provided a needle holder for handling the aforementioned surgical needle, i.e., a surgical needle having a tip portion and a clamping portion which are electrically connected, and a surface covered with an insulating material excluding the tip portion. The needle holder has conductive protrusions and a predetermined surface covered with an insulating material excluding the protrusion. The protrusions are electrically connected to a power source for applying a current. When the aforementioned surgical needle is clamped by this needle holder, the protrusions pierce through the insulating material so as to be electrically connected to the conductive member of the clamping portion of the surgical needle.

DETAILED DESCRIPTION OF THE PREFERRED EMBODIMENTS

Hereinafter, explanation will be given on a surgical needle with its configuration, a method for producing the surgical needle as well as a needle holder according to the present invention.

Figure 1:
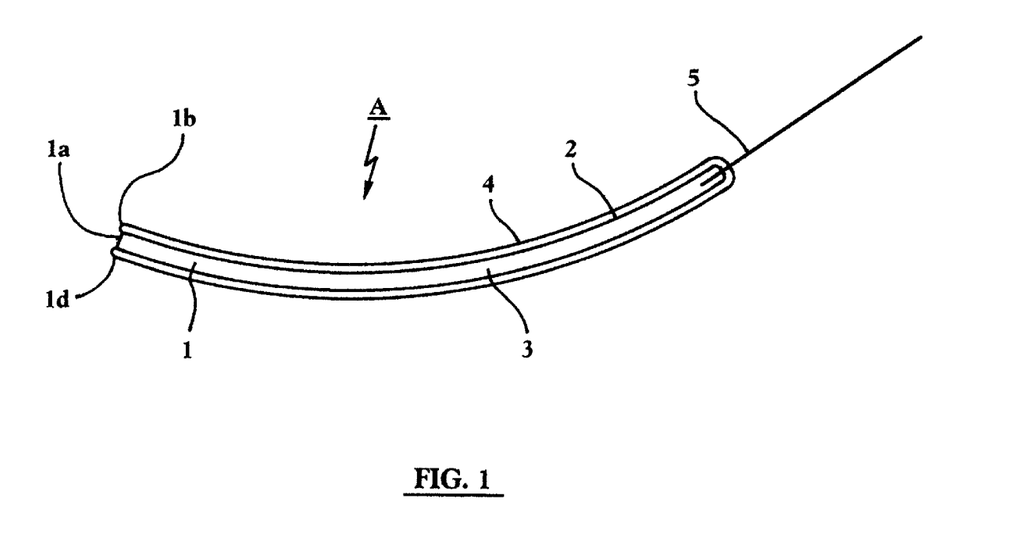
FIG. 1 is a longitudinal cross sectional view of a surgical needle.
Figure 2:
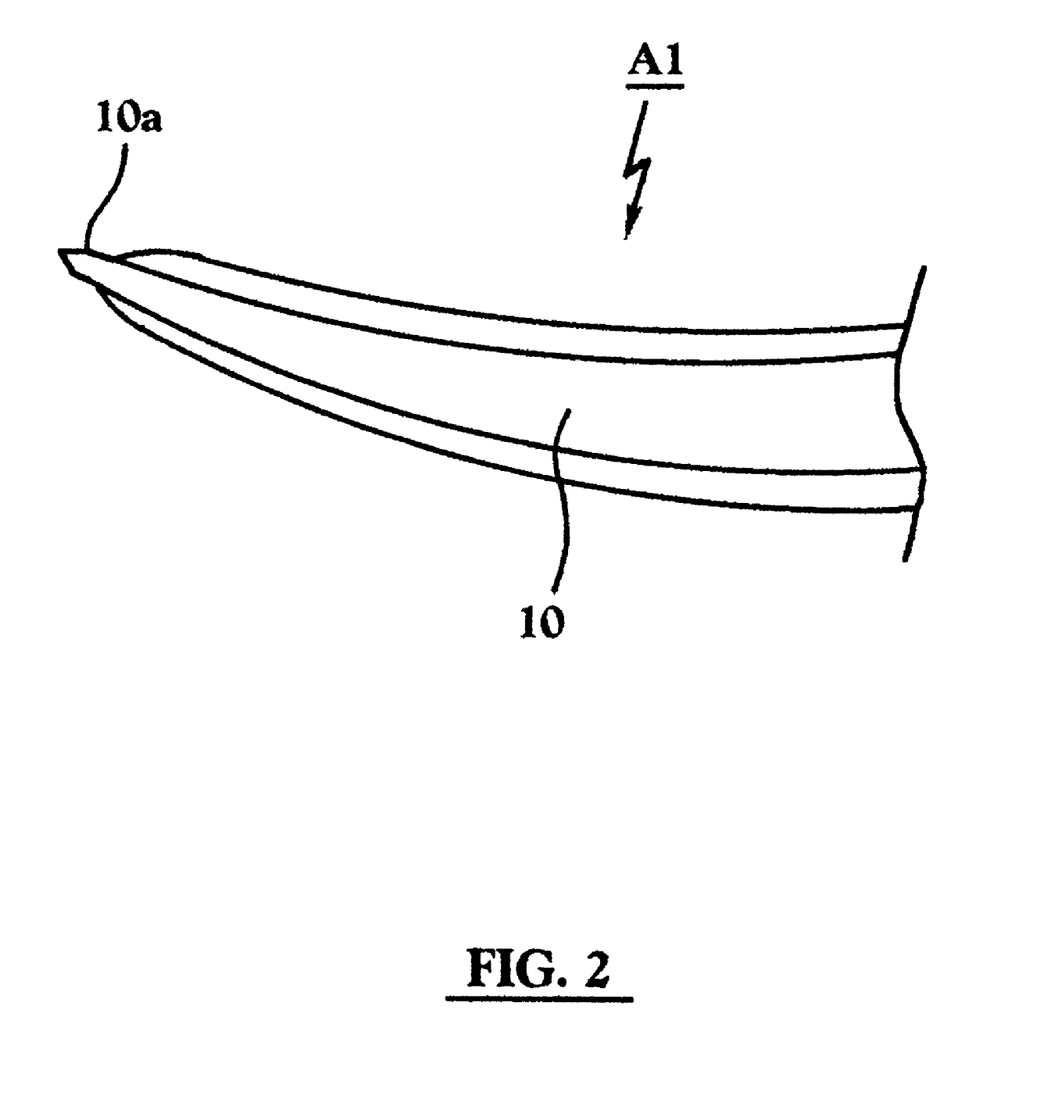
FIG. 2 is a cross sectional view of surgical needle having a tip portion of a modified configuration.
Figure 3A:
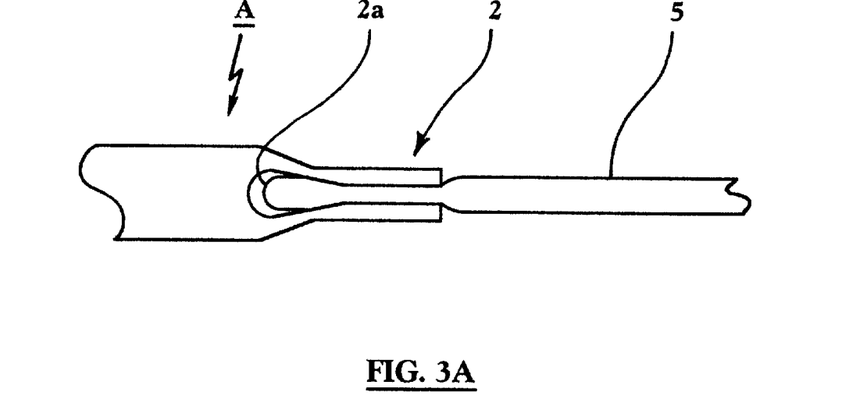
FIGS. 3(a)–(c) is a schematic view showing some structural examples of a suture coupling portion.

Firstly, a configuration of the surgical needle will be explained with reference to FIG. 1 to FIG. 4. FIG. 1 is a longitudinal cross sectional view of a surgical needle; FIG. 2 is a cross sectional view of surgical needle having a tip portion of a modified configuration; FIG. 3 shows some structural examples of a suture coupling portion; and FIG. 4 shows a position where the suture coupling portion is formed.

A surgical needle according to the present invention causes electric discharge between the surgical needle and a portion of the tissue to be sutured so that a gas (vapor) is generated in that portion of the tissue, which is destroyed to leave a vacancy for passing the surgical needle. Together with the surgical needle, an accompanying suture passes through the tissue to be sutured.

The surgical needle A according to an embodiment shown in FIG. 1 to FIG. 4 has a curved configuration having a circular cross section, and is made of a steel wire such as stainless steel wire and piano wire or a non-ferrous metal wire such as an aluminum alloy wire and a copper alloy wire, which is covered with an insulating material.

The surgical needle A has a tip portion 1 composed of a needle tip end 1a and a tip surrounding portion 1d made of an electrically insulating material; a suture coupling portion 2; and a needle body 3. The tip portion 1 is formed continuous to the needle body 3 which is a clamping portion to be clamped by the needle holder B when the surgical needle A is to be manipulated by a needle holder B (FIG. 9) which will be detailed later. The surgical needle A has a surface covered by an insulating layer 4 including the tip surrounding portion 1d and excluding the needle tip end 1a.

The needle body 3 may be significantly short. When it is almost 0, the tip portion 1 may be directly continuous to the suture coupling portion 2. In such a case, the suture coupling portion is the clamping portion to be clamped by the needle holder B.

The tip portion 1 includes the needle tip end 1a having an electric discharge function to a tissue of an organ and a needle end face 1b which includes the needle tip end. In the surgical needle A according to the present embodiment, the needle end face 1b does not have a sharp configuration but a blunt configuration such as a flat configuration or a hemisphere having a diameter not less than 1/10 of the diameter of the needle body.

The needle end face 1b is covered by the insulating layer 4 excluding its center portion, which serves as the needle tip end 1a. That is, the needle tip end 1a is electrically exposed and has an adequate area for surely causing electric discharge to a tissue. To assure this adequate area, the needle tip end 1a is surrounded by the tip surrounding portion 1d made of the insulating material.

As has been described, in the surgical needle A according to the present embodiment, the tip portion 1 has a needle end face 1b so as to form a blunt configuration, which prevents the surgical needle from readily sticking in surgical rubber gloves or fingertips. That is, with a normal manipulation load applied, the surgical needle A will not stick through a glove or clothing into a skin of the surgeons or their assistants. Consequently, even if a patient to be surgically operated is a carrier of bacteria and viruses which are infectious through blood, there is no risk that the surgeons or their assistants are susceptible to these infectious diseases through a very small amount of blood attached to the tip end of the surgical needle A.

The suture coupling portion 2 is a portion for connecting a suture 5. In a normal surgical needle as the surgical needle A shown in FIG. 1, the suture coupling portion 2 is formed at the opposite end of the surgical needle A.

FIG. 2 shows a modified configuration of the tip portion, i.e., a tip portion 10 of a surgical needle A1, which is tapered to form a sharp tip, Like the conventional surgical needle, the surgical needle A1 can penetrate into a tissue while cutting open the tissue. The insulating layer 4 is provided over the entire surface of the surgical needle A1 except the tip end of the tip portion 10, which serves as a needle tip end 10a.

Note that the surgical needle according to the present invention may not be curved but have a straight configuration. Moreover, the cross section thereof may not be circular but elliptic or polygonal.

FIG. 5 shows how the suture 5 is coupled to the suture coupling portion 2. FIG. 5 A shows the suture coupling portion 2 of the surgical needle A according to the present embodiment. This suture coupling portion 2 is formed a tail end of the surgical needle A, where a suture holding hole 2a is formed. An end of the suture 5 is inserted into the suture holding hole 2a, and then the suture holding hole 2a is squeezed.

Figure 3B:
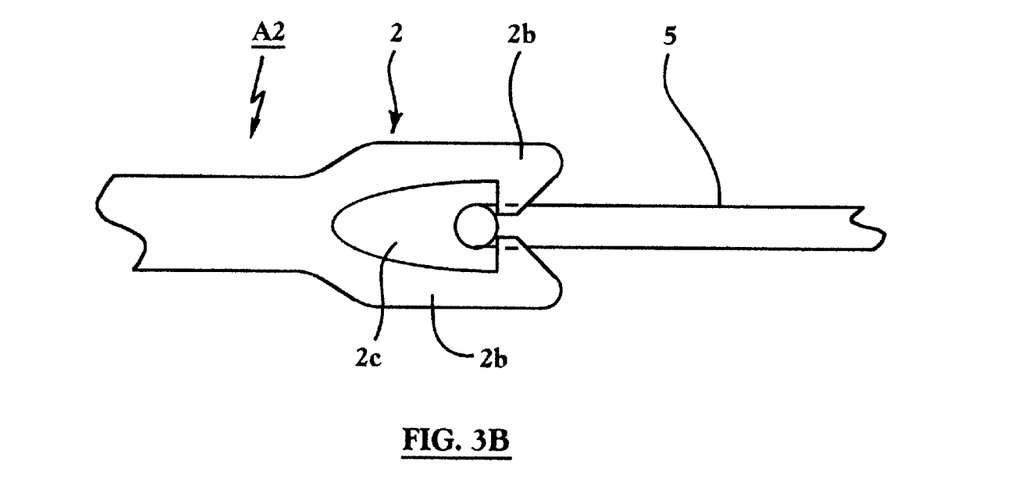
Figure 3C:
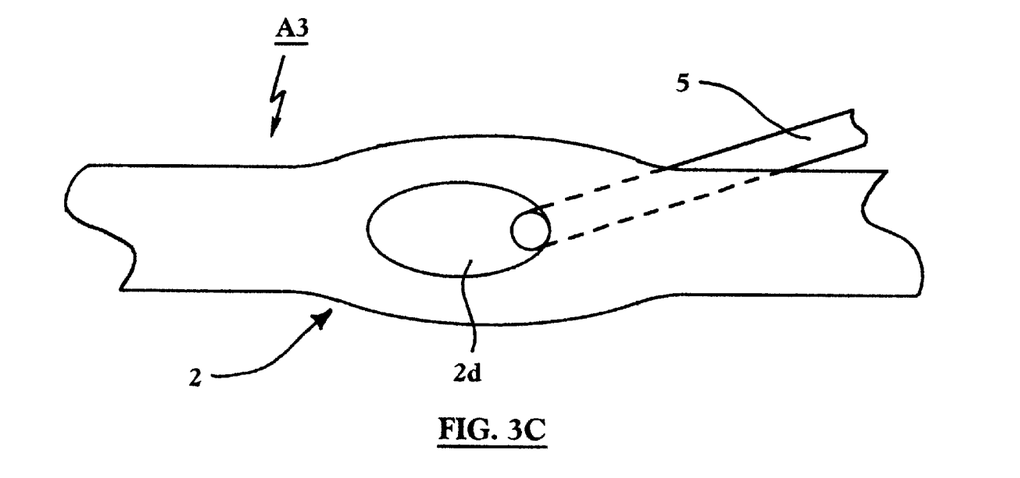

The suture coupling portion 2 may have configurations as shown in FIG. 3B and FIG. 3C. FIG. 3B shows a surgical needle A2 which has a pair of spring members 2b at a tail end opposite to the tip portion 1. The suture 5 is inserted into a through hole 2c defined by the pair of spring members 2b, so as to be coupled to the surgical needle A2. Furthermore, FIG. 3C shows a surgical needle A3 which has a through hole 2d at a predetermined position of the needle body. The suture 5 is inserted through this through hole 2d so as to be coupled to the surgical needle.

Figure 4A:
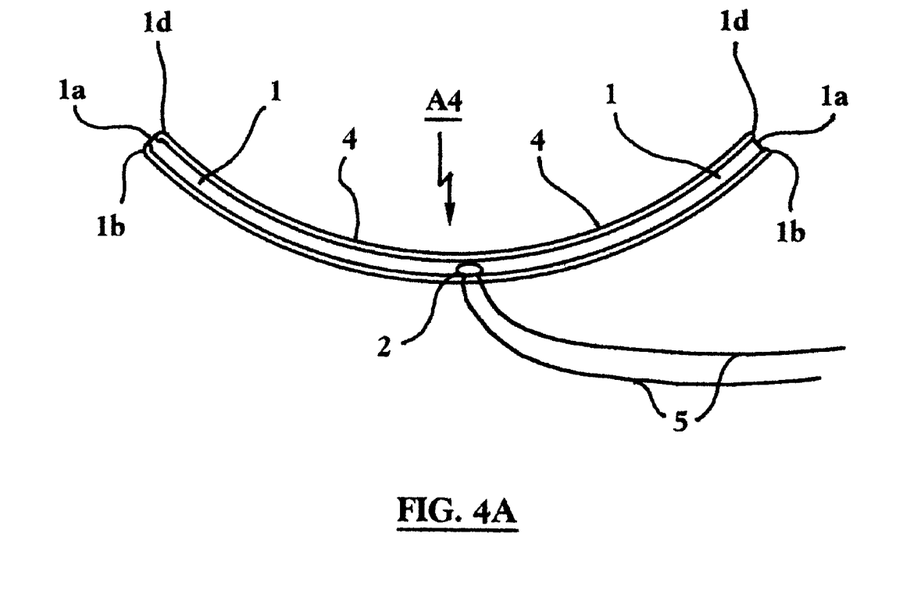
FIG. 4 shows a position where the suture coupling portion is formed.
Figure 4B:
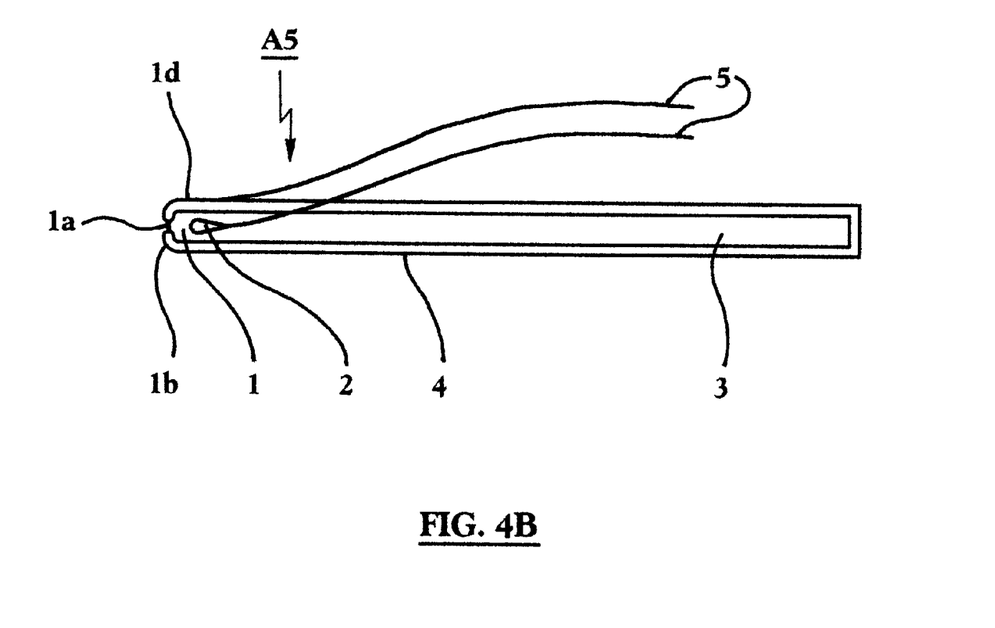

FIG. 4A shows a surgical needle A4 which is used for successive suturing. The suture coupling portion 2 thereof is formed almost at a center of the needle body so that both ends of the needle body are provided with a needle tip end electrically exposed. FIG. 4B shows a surgical needle A5 which has a suture coupling portion at the same end portion as the tip portion 1. Thus, the suture coupling portion 2 is not always provided at a tail side as in the surgical needle A but may be provided at various positions depending on the purpose of the surgical needle. This also brings about a case where the needle tip end is provided at both ends of the needle body.

This insulating layer 4 has a purpose of preventing discharge between the surgical needle except for the needle tip and a tissue of an organ, and is provided over a surface of the surgical needle 4 including the tip surrounding portion 1d and excluding the needle tip 1a of the tip portion 1. Consequently, when the surgical needle A is held by a surgeon and approached to a portion of a tissue to be sutured and a high frequency current is applied to the surgical needle A to cause discharge between the needle tip 1a and the portion of the tissue, no discharge is caused between the surgical needle A excluding the needle tip 1a and the tissue.

Note that the insulating layer 4 is preferably provided over the entire surface excluding the needle tip 1a so as to prevent discharge from the surgical needle except for the needle tip 1a. Especially, the tip surrounding portion 1d should be covered with the insulating layer 4. However, the insulating layer 4 need not be provided for a portion which will not be in contact with the tissue when the surgical needle A sticks into the tissue and which is not to be clamped by the needle holder so as to be electrically conductive.

The insulating layer 4 is not limited to a particular material but may be formed by selectively using various materials including a synthetic resin such as polyethylene resin and tetrafluoroethylene resin or an inorganic material such as ceramics. It should be noted the type of the surgical needle A can easily be identified by a color of the insulating layer 4 or a mark printed or engraved on the insulating layer 4 according to the specification of the surgical needle A. It is also possible to identify respective positions of the surgical needle by changing the color of the insulating layer according to the positions, for example, a tip surrounding portion, a clamping portion, and a tail portion of a surgical needle. Moreover, it is possible to select a material which can be subjected to sterilization, such as oxide gas (EOG) sterilization, vapor sterilization and electron beam sterilization. It is also possible to make the insulating material bacteria-resistant.

Furthermore, when the surgical needle A sticks into a tissue the surface of the insulating layer 4 tends to restore its configuration, causing a friction with the tissue. It is preferable that the insulating layer 4 is made from a material having a low friction coefficient with a tissue. As a material having a low friction coefficient with a tissue and having no adverse effect to the tissue, there can be exemplified silicon, tetrafluoroethylen resin or the like.

Moreover, the insulating material applied to the tip surrounding portion is preferably made from a heat-resistant material so as to be endurable to a heat generated when a cavity is formed in the tissue. The insulating material which is heat-resistant may be applied not only for the tip surrounding portion but also for the clamping portion. It is preferable that the material be resistant to a heat of about 250° C., but the material having a lower heat resistance can also be used.

When the surgical needle A is clamped by the needle holder B which will be detailed later, the insulating layer 4 is locally deformed and pierced by the protrusions of the needle holder B or, if the insulating layer 4 is hard, it is locally cracked, so that the surgical needle A electrically in contact with the needle holder through the crack. Consequently, it is preferable that the insulating material 4 be either a soft material which can easily be pierced or a hard material having such configuration that enables to readily cause a crack.

In a case when the insulating layer 4 is made from a soft material such as polyethylene or vinyl, the insulating layer 4 can easily be pierced by the protrusions formed on the needle holder. Thus, even is the insulating layer 4 is provided over the surface of the surgical needle A, a portion clamped by the needle holder B becomes electrically conductive through the protrusions of the needle holder B (see FIG. 10). Moreover, when a soft material is used to form the insulating material 4, there is an advantage that the surgical needle A with the insulating material 4 may be curved to adjust configuration thereof. Another advantage is that when the clamping by the needle holder B is released, the soft material exhibits a restoration strength which closes the pierced hole to a certain degree. This prevents electric leak when the surgical needle A is manipulated by clamping at another position of the surgical needle A.

In a case when the insulating layer 4 is made from a hard material such as ceramics, it is preferable that the force to attach the insulating layer 4 to the needle body 3 be sufficiently small so that there can easily be caused a crack when an external force is applied.

Furthermore, the insulating layer 4 may be made from such a material or may be formed into such a configuration that the insulating property thereof is locally eliminated when a pressure is applied. Moreover, the insulating layer 4 may be made from a material having a piezoelectric effect which is an insulator in a normal state and, only when an external force is applied, the ion crystal causes dielectric polarization in accordance with the stress. In this case, the needle holder need not have any protrusion. When the cramping by this needle holder is released, the insulating material becomes an insulator, thus preventing a leak.

In the above-described embodiment, explanation has been given on a configuration of the surgical needle A made by using a metal wire having conductivity. However, it is also possible to form a surgical needle from a material having an insulating property such as ceramics and bakerite, through which a conductive wire is embedded. In this case, the surgical needle may have such configuration that a portion is predetermined so as to serve as a clamping portion to be clamped by the needle holder. The clamping portion is made a conductive portion electrically connected to the wire and the clamping portion is further covered by an insulating layer.

It should be noted that when the tissue to be operated is a hard tissue such as a bone, there is a case when a metal suture is used as a surgical needle. An end of this metal suture may be embedded in the aforementioned surgical needle so as to serve as the aforementioned wire.

Figure 5A:
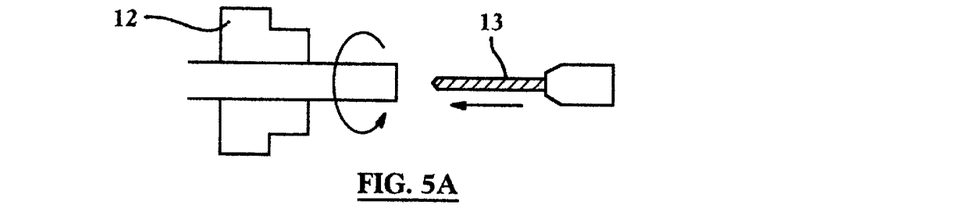
FIG. 5 shows a method for producing the surgical needle.
Figure 5B:
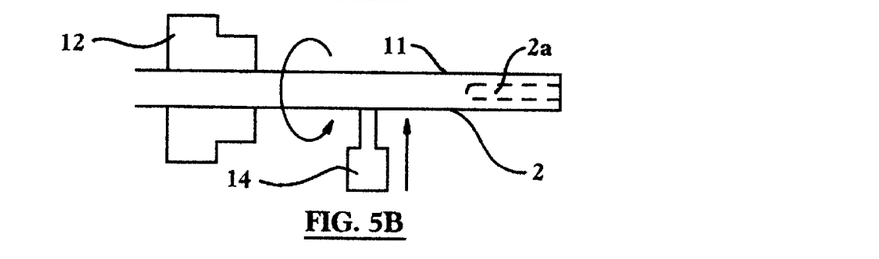
Figure 5C:
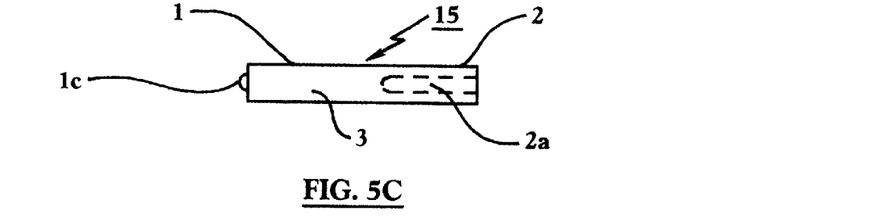
Figure 5D:
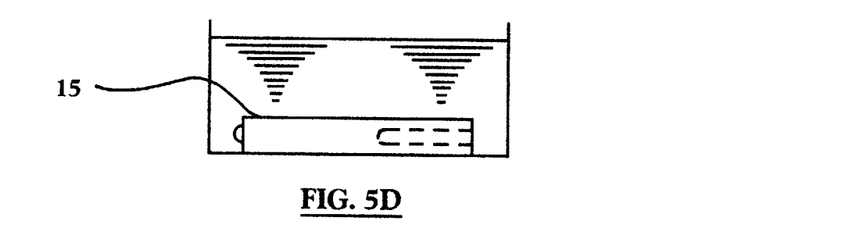
Figure 5E:
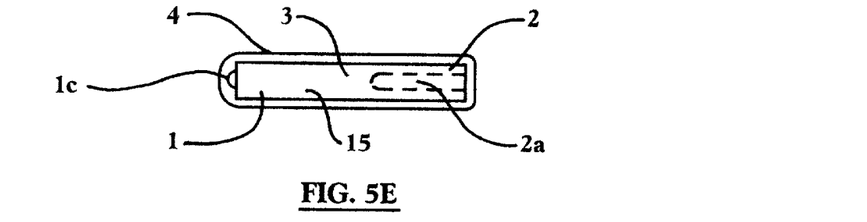
Figure 5F:
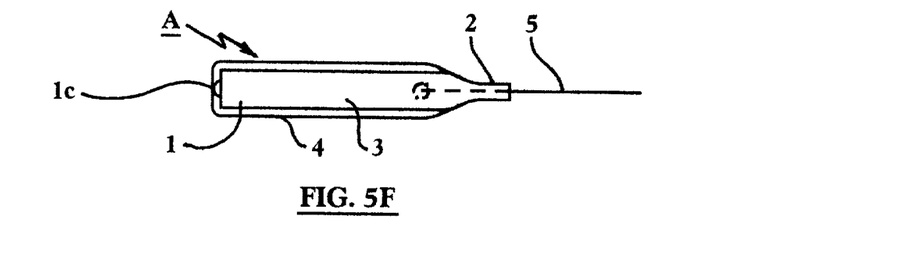
Figure 6:
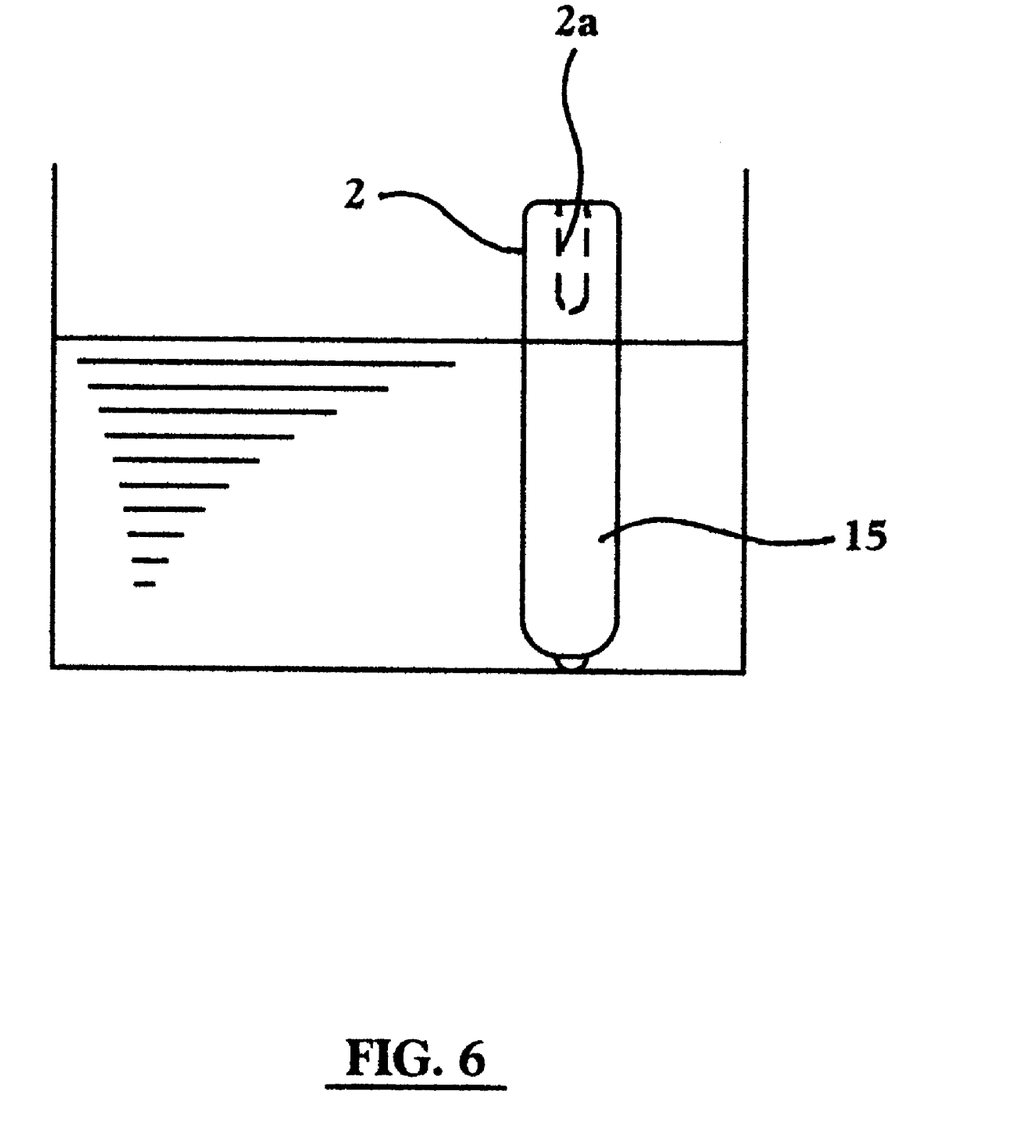
FIG. 6 shows another method for producing the surgical needle.
Figure 7:
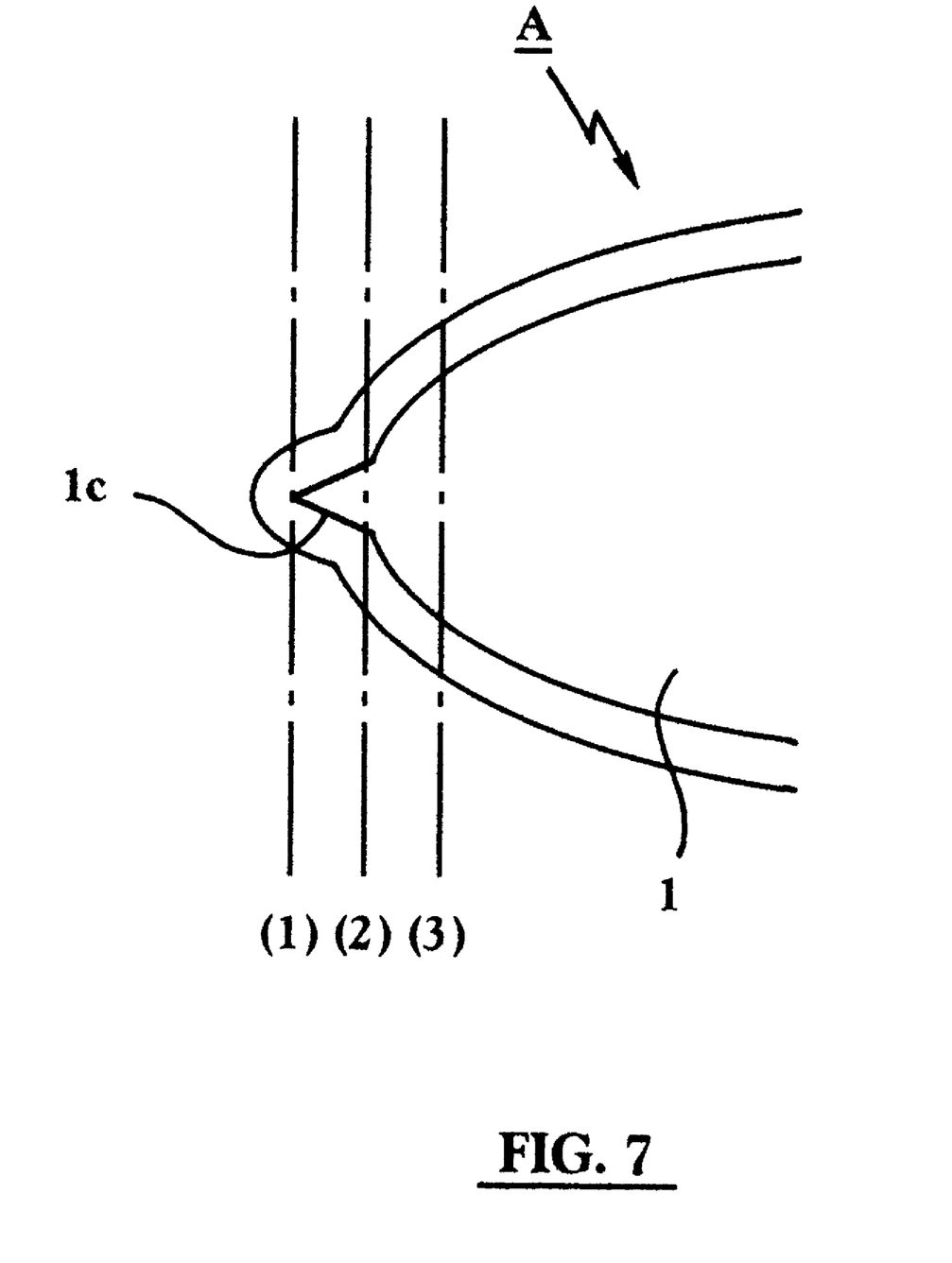
FIG. 7 shows a portion of a needle tip end to be cut off.
Figure 8A:
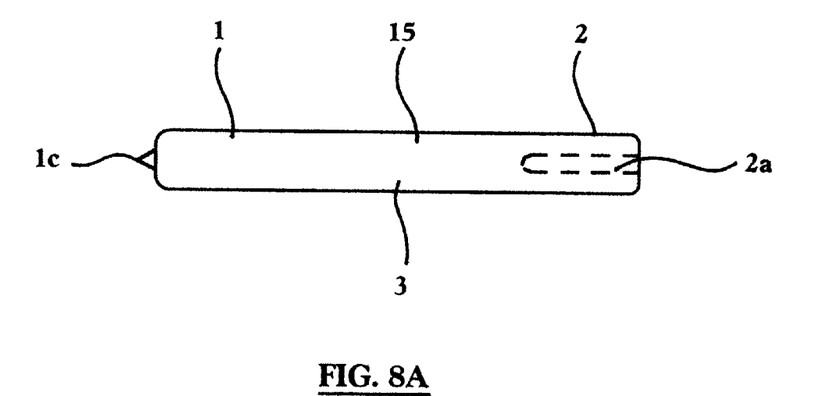
FIG. 8 shows still another method for producing the surgical needle.
Figure 8B:
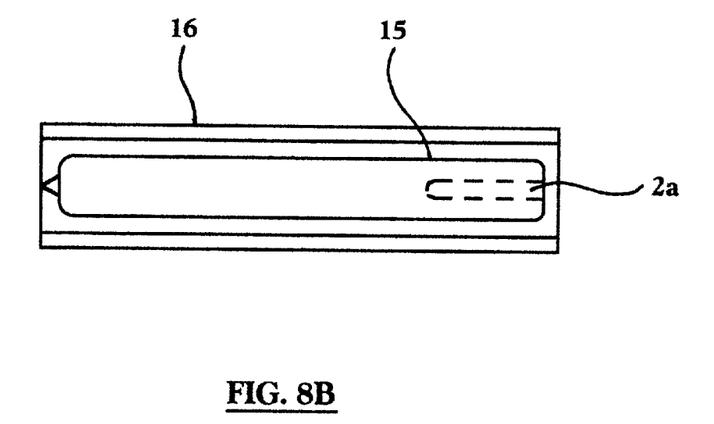
Figure 8C:
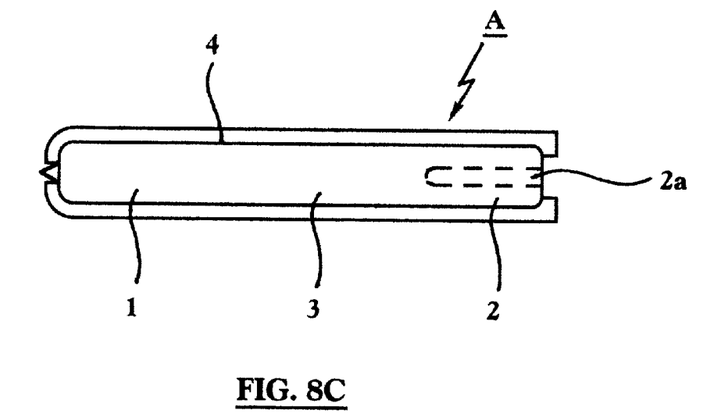

Description will now be directed to a method for producing the surgical needle A and a conventional surgical needle, i.e., a surgical needle having a needle tip electrically exposed and capable of discharge, with reference to FIG. 5 to FIG. 8. FIG. 5 shows a method for producing the surgical needle. FIG. 6 and FIG. 8 show other methods for producing the surgical needle. FIG. 7 shows a portion of a needle tip end to be cut off. Note that explanation on the needle curving step and the thermal processing step which are actually required is omitted in the explanation given below on the production procedure of the surgical needle.

As shown in FIGS. 5A to 5C, a metal wire 11 to be made into the surgical needle A is held by a chuck 12 of an automatic lathe, and, by using a drill 13, a suture holding hole 2a is formed so as to form a suture coupling portion 2 at an end of the metal wire 11. Next, by using a turning tool 14, the metal wire 11 is cut at a predetermined position so as to obtain a needle material 15 having a tip portion 1 at the opposite side of the suture coupling portion 2 and a needle body 3 between thereof.

In this step, a protrusion 1c is formed at the center of the end portion of the needle material 15 which has been separated from the metal wire 11 by way of rotational cutting using the automatic lathe. The needle material 15 is required to be subjected to grinding so as to remove the protrusion 1c.

Next, the insulating layer 4 is formed over the needle material 15. This step requires a process according to the property of the material forming the insulating layer 4. For example, when forming the insulating layer 4 by silicone, the needle material 15 is dipped in a silicone solution as shown in FIG. 5D and, after taken out of the silicone solution, cured to form the insulating layer 4 as shown in FIG. 5E. It is also possible, as shown in FIG. 6, not to dip the entire needle material 15 in the silicon solution, i.e., not to form an insulating layer over the suture coupling portion so as not to close the suture holding hole 2a. Moreover, considering the type and thickness of the insulating material, it is also possible to employ deposition or electrocoating.

As shown in FIG. 5F, a suture 5 in inserted through the suture holding hole 2a formed in the suture coupling portion 2 of the needle material 15 and a portion corresponding to the hole 2a is squeezed so as to couple the suture 5. Note that the needle material with the insulating layer over the suture coupling portion 2 which has been removed has the same function as the needle material without any insulating layer over the suture coupling portion from the beginning.

Moreover, as shown in FIG. 7, it is possible to electrically expose the end of the tip portion of the needle material by cutting off only the insulating layer 4 over the needle end or a predetermined thickness of the conductive needle material so as to form the needle tip end 1a. As shown in FIG. 7, by changing the thickness to be cut off, i.e., by changing the cutting off position from (1) to (3) in FIG. 7, it is possible to adjust an area of the needle tip end 1a. According to this method, the needle tip end 1a is contained on a plane of the insulating layer 4, which facilitates discharge.

As can be understood from the above description, the production method according to the present invention is not limited to the production of the surgical needle according to the present invention but can also be applied to a production of a surgical needle in general which has an electrically exposed needle tip end so that a high frequency current is flown between the needle tip end and a tissue of an organ to be pierced so as to form a cavity for advancing the surgical needle. For example, the production method can also be employed for producing a surgical needle having no insulating material over a clamping portion.

FIG. 8 shows another production method for producing the surgical needle of the present invention, although the method does not fall in the production method according to the present invention. According to the method shown in FIG. 8, the needle material 15 obtained in the same method as described above is covered by a sleeve 16 which has properties of insulation and heat contraction, so as to form the insulating layer 4.

That is, as shown in FIG. 8A, the needle material 15 is prepared in the same steps of the aforementioned method (FIGS. 5A to 5C) so as to have a protrusion 1c in the tip portion 1 and a suture holding hole 2a in the suture coupling portion 2. Next, as shown in FIG. 8B, the needle material 15 is inserted into a sleeve 16 formed, for example, from tetrafluoroethylene resin having insulation and heat contraction properties. Then, the sleeve 16 is heated so as to contract and form the insulating layer 4 over the needle material 15.

According to this method, by changing the length of the sleeve 16 and adjusting the portion of the needle material to be covered by the sleeve 16, it is possible to adjust the size of the needle tip en of the tip portion 1 as well as to form the insulating layer 4 over a desired portion of the needle material 15.

In either of the methods, the needle material is curved by using a roller so as to form a curved surgical needle as shown in FIG. 1.

Figure 9:
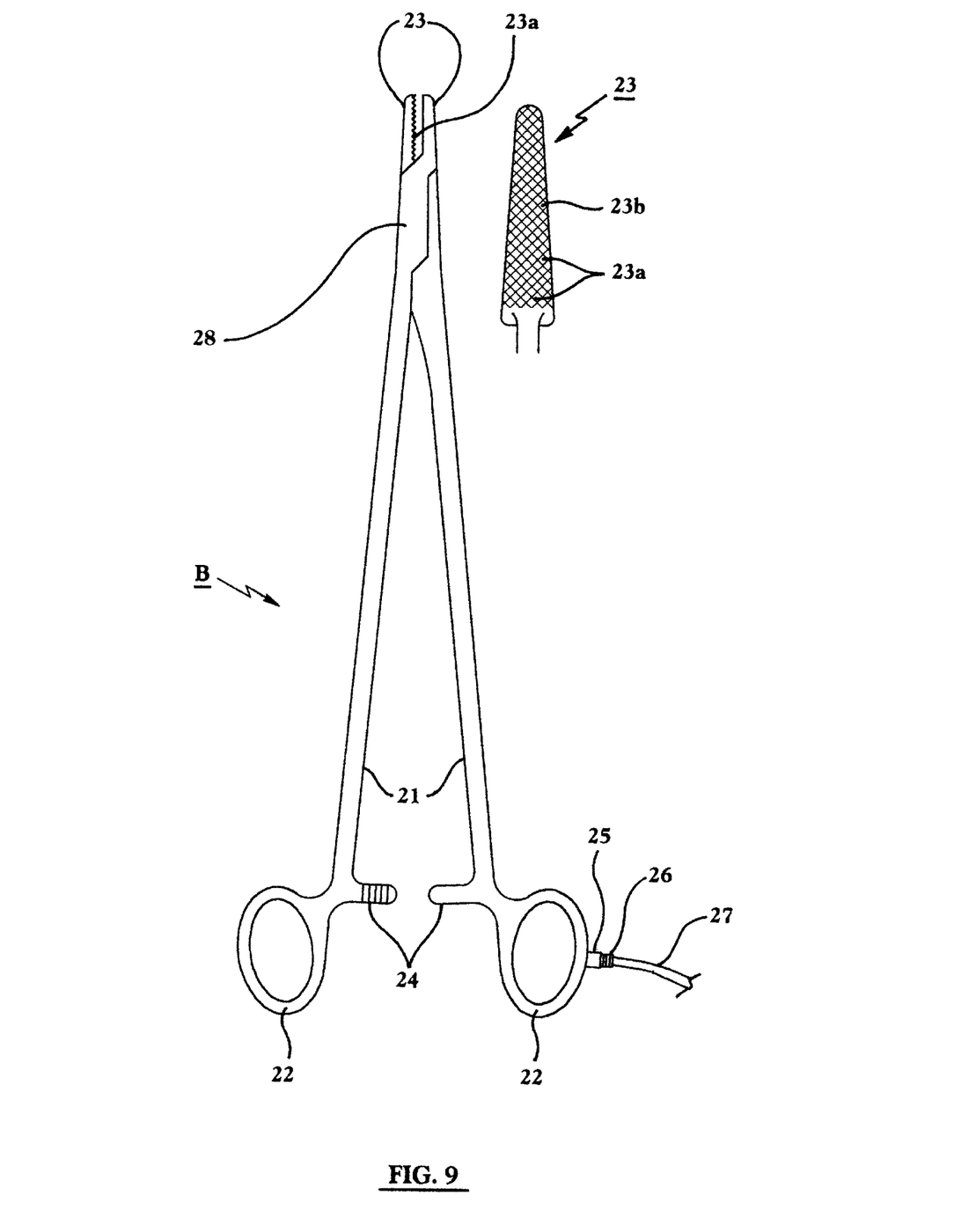
FIG. 9 is a front view of a needle holder.
Figure 10A:
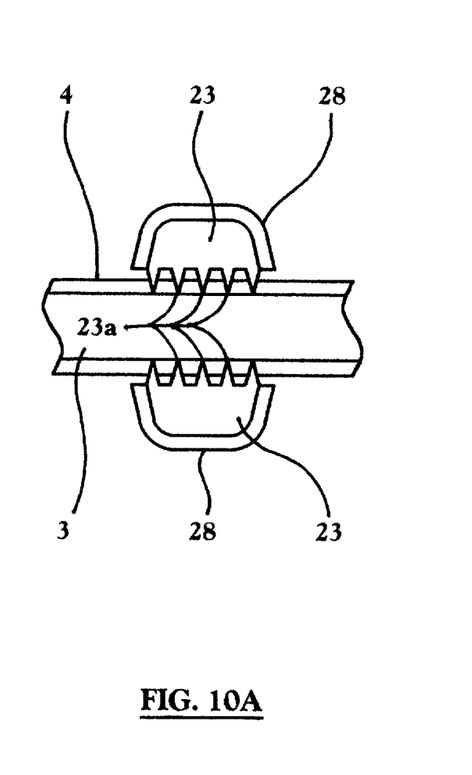
FIG. 10 shows a state when the surgical needle is clamped by the needle holder.
Figure 10B:
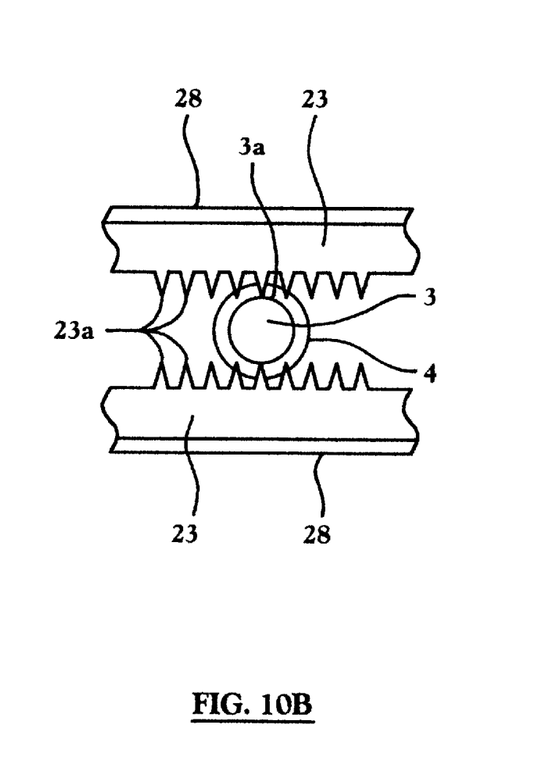

Description will now be directed to the needle holder according to the present invention with reference to FIG. 9 to FIG. 11. FIG. 9 is a front view of the needle holder; FIG. 10 shows a state of a surgical needle clamped by the needle holder; and FIG. 11 shows other configurations of the needle holder.

As shown in FIG. 9, the needle holder B is constructed so as to clamp the surgical needle A by rotationally moving a pair of levers 21 and apply a current to the surgical needle A. The pair of levers 21 is provided with a manipulation portion 22 at one end, into which a surgeon thrust his/her fingers for manipulation, and a clamping portion 23 for clamping the surgical needle A. The manipulation portion of the pair of levers 21 is provided with a stopper portion 24 for holding the pair of levers 21 in a closed sate of the needle holder B. One of the levers 21 is provided with a hand switch 25 and a terminal 26 at a predetermined position. The terminal 26 is connected to cord 27 which is connected to a high frequency electric source apparatus. The clamping portion 23 provided in each of the pair of levers is provided with a plurality of protrusions 23a.

If a discharge occurs between the needle holder B and a tissue of an organ, the tissue may be hurt. To avoid this, a predetermined surface of the needle holder B, at least portion which is brought into contact with the tissue or brought into a vicinity of the tissue, requires to be insulated. For this, according to the present embodiment, the entire surface of the needle holder 23 excluding the protrusions 23a is coated by an insulating material (such as tetrafluoroethylene resin) so as to form an insulating layer 28. It is preferable that a sufficient insulating layer 28 be formed over the entire surface of the needle holder B, especially over the clamping portion 23 which has a high possibility to be brought into contact with a tissue of an organ during a surgical operation, excluding the protrusions 23a or clamping faces 23b on which the protrusions 23a are formed.

Explanation will be given with reference to FIG. 10 on a function of the protrusions 23a. When the surgical needle A is clamped by the clamping portion 23 of the needle holder B, the protrusions 23a pierce into the insulating layer 4 formed on a surface of the needle body 3 and their tips are brought into contact with a circumferential surface 3a of the needle body 3. Then, by depressing the hand switch 25 or a foot switch (not depicted), it is possible to apply a high frequency current to the surgical needle A. Note that since the protrusions 23a pierce through the insulating layer 4, the surgical needle A will not move with respect to the needle holder B when the surgical needle A is manipulated by applying a strength. Thus, clamping of the surgical needle A by the needle holder B is assured.

It should be noted that the protrusions 23a may have configurations other than those shown in FIG. 9 and FIG. 10 as long as the configuration exhibits a piercing ability. For example, if the insulating layer 4 is made of a soft material easy to be pierced, a protrusion may have a blunt tip having a trapezoidal cross section, thus increasing the contact area with the external circumferential surface 3a of the needle body 3.

Figure 11A:
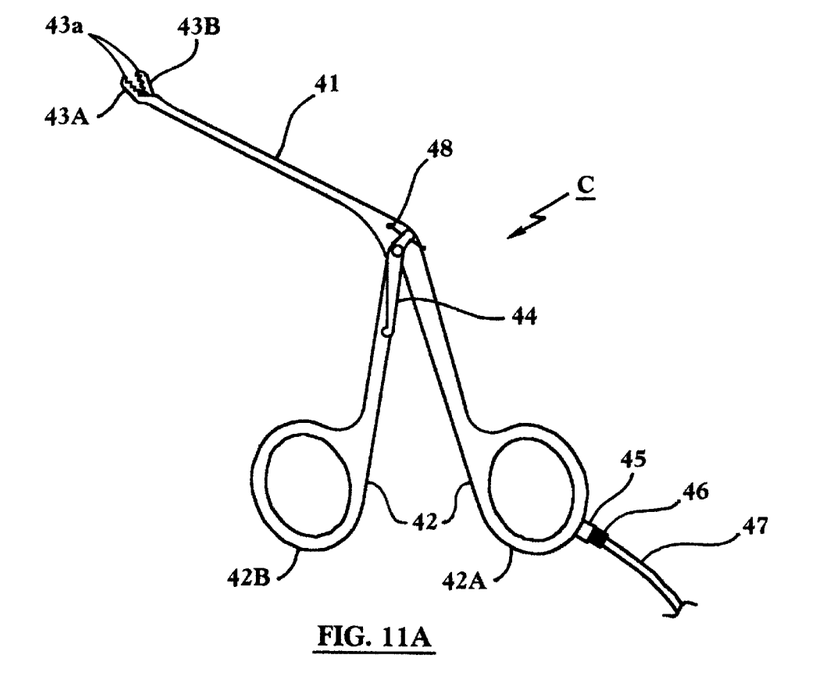
FIG. 11 shows modified configurations of the needle holder.
Figure 11B:
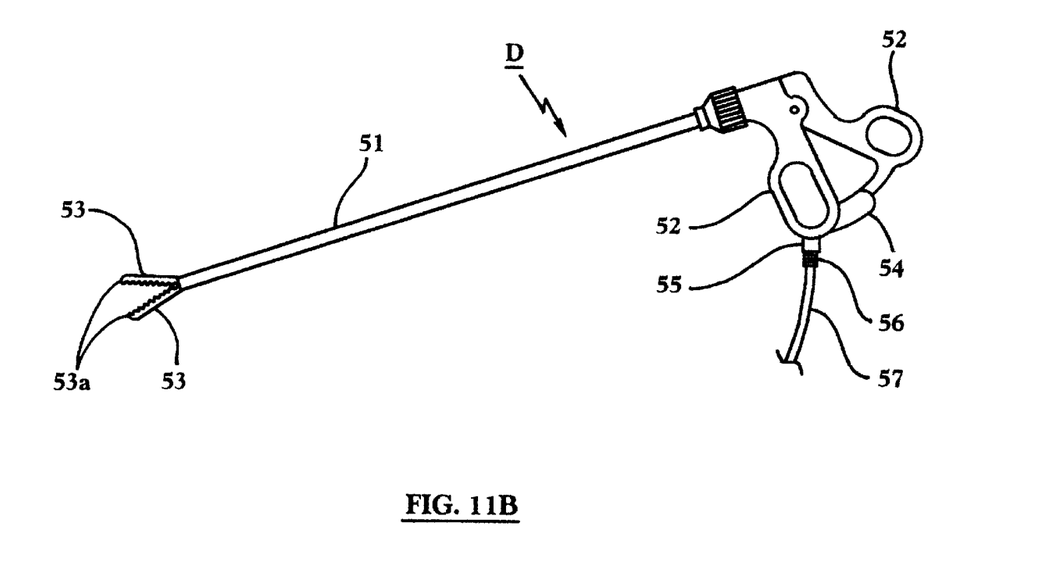

The needle holder B shown in FIG. 9 is a forceps type which is generally used. However, configuration of the needle holder is not limited to this configuration but can be modified into other configurations as shown in FIG. 11. FIG. 11A shows a needle holder C of forceps type which is used by otolaryngologists, and FIG. 11B shows a needle holder D of forceps type used in endoscopic operation.

As shown in these drawings, each of the needle holders C and D has an operation portion 42, 52 at one end of a rod 41, 51 and a stopper portion 44, 54 formed in manipulation portion 42, 52 so as to maintain a needle clamping state. Similarly as the needle holder B, a hand switch 45, 55 and a terminal 46, 56 is formed, which is to be connected to a cord 47, 57 for connection to a high frequency electric source apparatus. Note that in the needle holder C, a clamping member 43A of the clamping portion 43a and a manipulation member 42A of the manipulation portion is formed together with the rod 43 as a unitary block. The other clamping member 43B is interlocked with the other manipulation member 42B through a shaft 48.

In each of the needle holders C and D, a plurality of protrusions 43a, 53a are formed in the clamping portion 43, 53. Moreover, in the same way as the aforementioned needle holder B, the surface of the needle holder C, D is coated by a fluorine coating for insulation, excluding the protrusions 43a, 53a.

It should be noted that the aforementioned needle holders B, C, and D are made from a metal material, which is covered by an insulating coating afterwards. However, it is also possible to form a main body of the needle holder from a non-conductive material such as plastic and ceramic, and to embed an electric wire connecting between the terminal fixed to the manipulation portion and the protrusions. In the needle holder according to the present invention, the protrusions may also be connected directly to a cord from a power source.

Figure 12:
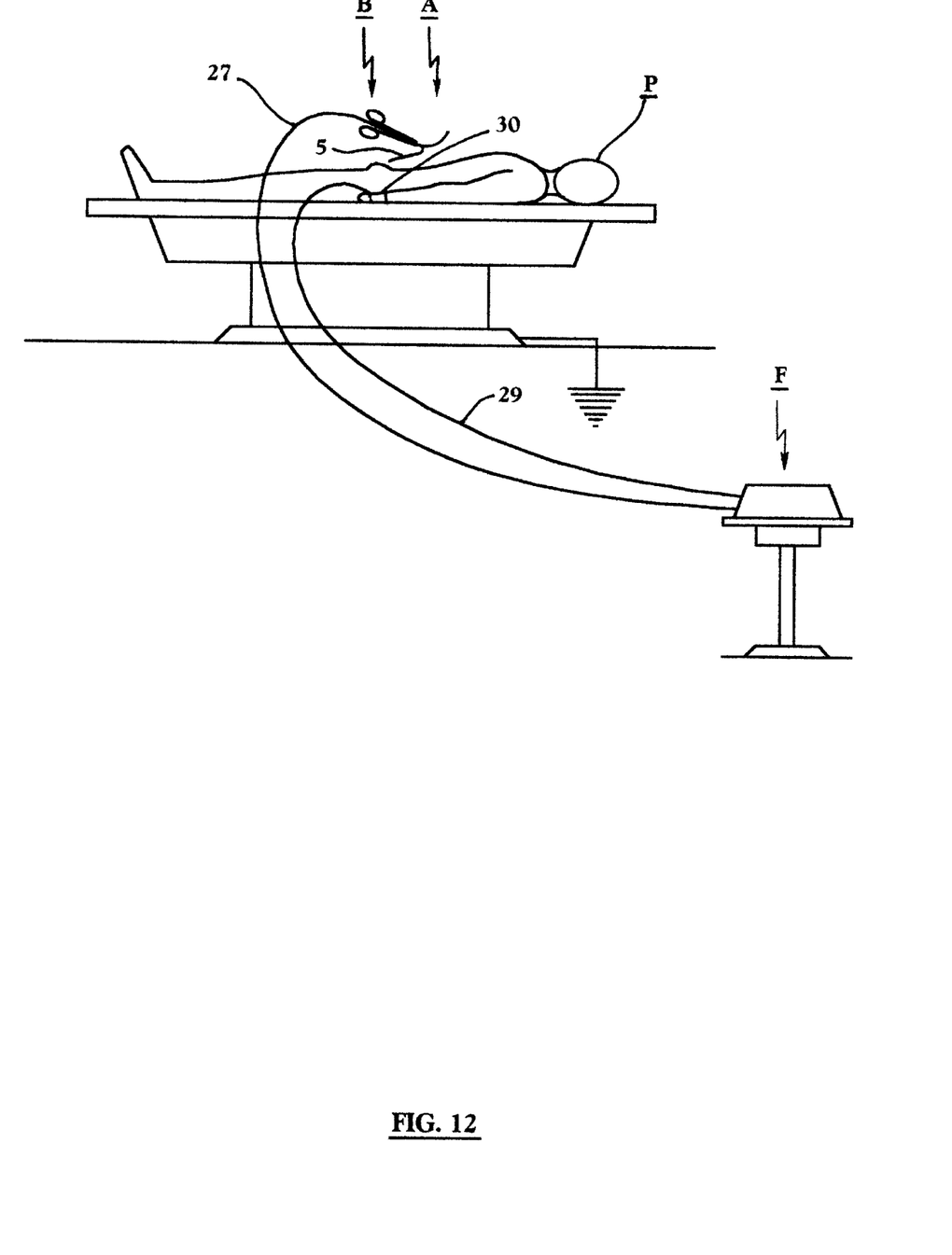
FIG. 12 is a schematic view explaining a configuration of a surgical apparatus using the surgical needle and the needle holder.
Figure 13:
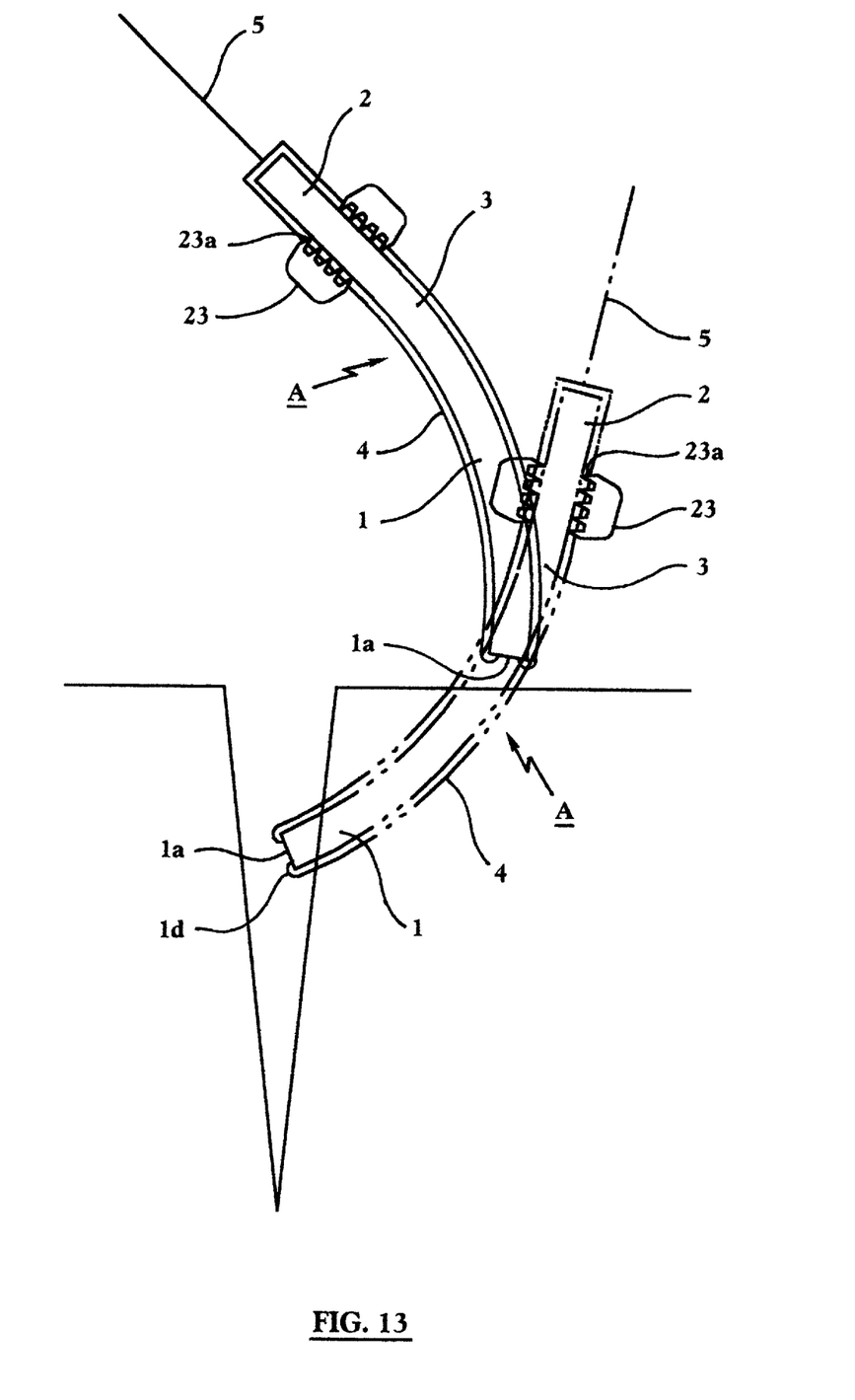
FIG. 13 is a schematic view explaining a state when the surgical needle passes through a tissue of an organ.

Description will now be directed to a procedure of tissue suturing in a patient with reference to FIG. 12 and FIG. 13. FIG. 12 shows an operation apparatus configuration using the aforementioned surgical needle and the needle holder; and FIG. 13 shows a state how the surgical needle passes through a tissue.

Firstly, as shown in FIG. 12, a power source F is connected to the surgical needle A and a patient P. The power source F is an AC high frequency electric source. The power source F is connected through a cord 27 to the needle holder B. The power source F is also connected through a cord 29 to a counter electrode plate mounted on the body of the patient P. Then, the surgical needle A is clamped with the needle holder B so that, as shown in FIG. 13, the protrusions 23a of the clamping portion 23 of the needle holder B pierce through the insulating layer 4, reaching the external circumferential surface 3a of the needle body 3 of the surgical needle A.

The needle tip portion 1a of the surgical needle A is positioned toward a particular portion of the tissue to be sutured and the hand switch 25 or a foot switch (not depicted) is turned on to apply a current to the surgical needle A. In this state, electric current flows from the power source F through the cord 27, the needle holder B, the surgical needle A, the patient P, the counter electrode plate 30, and further through the cord 29 back to the power source F so as to be electrically short-circuited, and a high frequency current is applied to this circuit.

When a current is applied to the surgical needle A, discharge occurs between the needle tip portion 1a and the tissue so that a water content in the particular portion of the tissue is explosively distilled to destroy the tissue of that particular portion, forming a vacancy. The needle tip portion 1a is protruded into this vacancy, thus maintaining a renewed distance between the needle tip portion 1a and the tissue. Thus, a discharge is successively caused between the surgical needle A and the tissue. As a result, the surgical needle A can be successively advanced into the tissue by applying only a small force to the surgical needle A.

The position of the surgical needle A to be clamped by the needle holder B can be selectively determined by a surgeon according to the type and configuration of the tissue, so as to facilitate the surgical operation.

In FIG. 13, the two-dot chain line shows a state of the needle tip portion 1a which has passed through out of the tissue, when the discharge between the needle tip portion 1a and the tissue terminates. In this state, no discharge occurs between the tissue and a portion of the surgical needle A remaining in the tissue, because of the insulating layer 3. Consequently, the tissue will not be hurt other than the hole portion through which the surgical needle A passes. Moreover, since the surgical needle A passes through a hole formed by discharge, there is only a small contact resistance between the shrinked tissue and the surgical needle A, and the surgeon can advance the surgical needle A with a small force.

When the needle tip portion 1 has come out of the tissue, the surgeon turns off the hand switch of the needle holder B or the foot switch so as not to apply a high frequency current. Then, the surgeon clamp again, with the needle holder B, the needle tip portion 1 which has come out of the tissue and pulls up the surgical needle A entirely out of the tissue.

It should be noted that a current flows from the needle tip portion 1 only to the tissue of the patient's body which is electrically connected to the power source F. When the surgeon erroneously touches the needle tip portion 1 of the surgical needle A, no current flows between them which may cause a danger of piercing the surgical needle A into a finger of the surgeon. Especially, the surgical needle A according to the present invention has a needle end face 1b of blunt configuration in the needle tip portion 1 and cannot pierce into the skin of the surgeon by normal operation load.

As has thus far been described, the present invention provides a surgical needle having in which a clamping portion is covered by an insulating material and only the portion which is has been actually clamped becomes conductive does not limit the clamping portion to a small range and facilitates manipulation during a surgical operation. Moreover, because the surface including the tip surrounding portion and the clamping portion excluding a portion clamped by a needle holder is covered by an insulating material, there will not be caused a leak, which may deteriorate the ability of the needle to pierce into a depth of a tissue of an organ.

Furthermore, in the surgical needle production method according to the present invention, the insulating material over the tip portion including at least the needle tip end is removed so as to be electrically exposed. Consequently, this method enables to readily produce the aforementioned surgical needle according to the present invention as well as the conventional surgical needle disclosed in Japanese Patent Laid-Open Hei 9-19436. Thus, a high productivity can be obtained. Moreover, the needle holder having protrusions enables to pierce through the insulating layer of the surgical needle, reaching the needle body so as to apply a current to the surgical needle. Thus, a conductive contact between the surgical needle and the needle holder can be obtained at a desired position of the needle body.

What is claimed is:

1. A surgical needle comprising a needle tip end and a clamping portion to be clamped by a needle holder for applying a current, said surgical needle having
   a conductive material provided at said needle tip end and
      a conductive material provided in said clamping portion which is electrically connected to the conductive material of said needle tip end, wherein
   an insulating material is provided over said clamping portion and a tip surrounding portion of said surgical needle, and said conductive material of said clamping portion is electrically connected to said needle holder when said insulating material over said clamping portion is clamped by said needle holder.

2. A surgical needle as claimed in claim 1, wherein said needle tip end has a blunt shape so as not to pierce into a tissue of an organ.

3. A surgical needle as claimed in claim 2, wherein said needle tip end has a surface of a cross section which orthogonally intersects the longitudinal direction of said surgical needle.

4. A surgical needle as claimed in claim 1, wherein the conductive material of said needle tip end and the conductive material of said clamping portion are constructed as a unitary metal wire in one body.

5. A surgical needle as claimed in claim 1, wherein said insulating material is formed from a synthetic resin.

6. A surgical needle as claimed in claim 5, wherein said insulating material is formed from an elastic resin which has a restoration force to close a hole made in the said insulating material.

7. A surgical needle as claimed in claim 1, wherein said insulating material is formed from an inorganic material such as ceramics.

8. A surgical needle as claimed in claim 1, wherein said insulating material is colored in a different color according to a type of surgical needle.

9. A method for producing a surgical needle having a needle tip end which is electrically exposed and a clamping portion a conductive material of which is electrically connected to a needle holder, when said clamping portion is clamped by said needle holder for applying a current, said method comprising:

a first step of covering a surface of said surgical needle at least including the needle tip end with an insulating material; and a second step of removing said insulating material at least from said needle tip end so as to be electrically exposed.

10. A method for producing a surgical needle as claimed in claim 9, wherein said second step is realized by cutting off a predetermined portion of said needle tip end with a plane which orthogonally intersects in the longitudinal direction of said surgical needle.

11. A method for producing a surgical needle as claimed in claim 10, wherein said needle tip end is formed into a tapered shape so that an electrically exposed area can be adjusted by changing a cutting position.

12. A needle holder for manipulating a surgical needle having a needle tip end which is electrically connected to a clamping portion to be clamped by said needle holder and covered by an insulating material excluding at least said needle tip end, wherein electrically conductive protrusions are formed in a portion of said needle holder which has a surface formed by an insulating material excluding said protrusions, and said protrusions are electrically connected to a power source for applying a current, so that when said surgical needle is clamped by said needle holder, said protrusions pierce through an insulating material of said clamping portion reaching a conductive material of said clamping portion so as to establish an electrical connection.

* * * * *